United States Patent

Baker et al.

[11] Patent Number: 5,525,327
[45] Date of Patent: Jun. 11, 1996

[54] POLYMERIC X-RAY CONTRAST COMPOSITIONS CONTAINING IODINATED POLYMERIC BEADS AND MICROCRYSTALINE CELLULOSE

[75] Inventors: Edward J. Baker, Northumberland, England; Robert W. Lee, Gilbertsville, Pa.; Carl R. Illig, Phoenixville, Pa.; John L. Toner, Downingtown, Pa.

[73] Assignee: Sterling Winthrop Inc., New York, N.Y.

[21] Appl. No.: 227,415

[22] Filed: Apr. 14, 1994

[51] Int. Cl.$^6$ ................................. A61K 49/04
[52] U.S. Cl. ................. 424/9.45; 514/57; 514/717; 514/941; 514/942
[58] Field of Search .............. 424/5, 9.45; 514/54, 514/57, 717, 941, 942

[56] References Cited

U.S. PATENT DOCUMENTS

| | | | |
|---|---|---|---|
| 2,832,722 | 8/1958 | Singher | 167/95 |
| 4,069,306 | 1/1978 | Rothman | 424/4 |
| 4,120,946 | 10/1978 | Quemille et al. | 424/4 |
| 5,019,370 | 5/1991 | Jay et al. | 424/4 |
| 5,310,538 | 5/1994 | Bacon et al. | 424/5 |
| 5,312,616 | 5/1994 | Illig et al. | 424/5 |
| 5,318,768 | 6/1994 | Illig et al. | 424/5 |
| 5,326,552 | 7/1994 | Na et al. | 424/4 |
| 5,326,553 | 7/1994 | Illig et al. | 424/5 |
| 5,330,740 | 7/1994 | Illig et al. | 424/5 |
| 5,334,370 | 8/1994 | Josef et al. | 424/5 |
| 5,336,484 | 8/1994 | Bacon et al. | 424/5 |
| 5,340,564 | 8/1994 | Illig et al. | 424/9 |
| 5,342,605 | 8/1994 | Illig | 424/5 |
| 5,368,837 | 11/1994 | Baker et al. | 424/5 |

*Primary Examiner*—Gary E. Hollinden
*Attorney, Agent, or Firm*—Fish & Richardson

[57] ABSTRACT

Disclosed are x-ray contrast compositions for oral or retrograde examination of the gastrointestinal tract comprising iodinated polymeric, water-insoluble beads having a particle size of from about 0.01 to about 1000μ wherein said iodinated polymeric beads comprise a polymer containing repeating units of the formula (I)

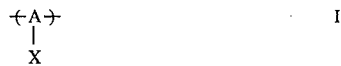

wherein

A is a repeating organic unit in the backbone chain of the polymer; and X is an organic moiety containing or iodinated eromatic group and a hydrophilic group, said moiety having an iodine content within the range of from about 40 to about 80 weight percent based or the molecular weight of X, in a pharmaceutically acceptable carrier comprising a cellulose derivative.

24 Claims, No Drawings

POLYMERIC X-RAY CONTRAST COMPOSITIONS CONTAINING IODINATED POLYMERIC BEADS AND MICROCRYSTALINE CELLULOSE

BACKGROUND OF THE INVENTION

1. Field of the Invention

This invention relates to an x-ray contrast composition for oral or retrograde administration to a mammal comprising water-insoluble iodinated polymeric beads as the contrast producing agent in a pharmaceutically acceptable carrier comprising a cellulose derivative.

2. Reported Developments

Roentgenographic examination utilizing x-rays and computed tomography (hereinafter CT) scans of fractures and other conditions associated with the skeletal system is routinely practiced without the use of contrast agents. X-ray visualization of organs containing soft tissue, such as the gastrointestinal (hereinafter GI) tract, requires the use of contrast agents which attenuate x-ray radiation. D. P. Swanson et al in "Pharmaceuticals In Medical Imaging", 1990, MacMillan Publishing Company, provides an excellent background in medical imaging utilizing contrast agents and compositions therewith.

The desiderata for an ideal GI contrast agent includes: good toxicological profile; the ability to fill the entire bowel/lumen and evenly coat the gut mucosa so that the presence of the bowel is detectable when the lumen is not distended; palatability and nonirritation to the intestinal mucosa; and passing through the GI tract without producing artifacts or stimulating vigorous intestinal peristalsis.

The most widely used contrast agents for the visualization of the GI tract is barium sulfate administered as a suspension orally or rectally as an enema. (See for example, U.S. Pat. Nos. 2,659,690; 2,680,089; 3,216,900; 3,235,462; 4,038,379 and 4,120,946) Notwithstanding its relatively good contrast characteristics, negligible absorption from the GI tract following oral or rectal administration and speedy excretion from the body, barium sulfate has certain disadvantages. In the presence of intestinal fluids, it lacks homogeneity which can result in poor x-ray images. In the colon, when administered as an enema, it flocculates and forms irregular clumps with fecal matter. The prior art considers as a serious problem the difficulty in achieving uniform adherence, and coating of, the mucosa of the GI tract by the water insoluble barium sulfate to provide high quality x-ray photographs. As a result of inadequate adherence to, and non-uniform coating of the mucosa, the x-ray results are often inferior, misleading to the practitioner and the imaging process must be repeated. It has also been observed that the barium sulfate, and other solid inorganic particulate radiopaque agents tend to settle out in the patient after evacuation but before and during x-ray imaging, which again deleteriously affects the quality of the x-ray pictures.

These drawbacks were addressed by many investigators and their efforts resulted in great improvements over the years. The drawbacks of unevenly coating of the mucosa with an insufficiently adherence thereto proved to be rather difficult to solve. To that end, the use of certain polymer additives were proposed as illustrated hereunder.

U.S. Pat. No. 4,069,306 discloses an x-ray contrast preparation which is said to adhere to the walls of body cavities. The preparation comprises a finely divided water-insoluble inorganic x-ray contrast agent and minute particles of a hydrophilic polymer which is insoluble in water but is water-swellable. The body cavity is supplied with such preparation suspended in water. The x-ray contrast agent is present in admixture with and/or enclosed in and/or adhered to said minute polymer particles.

U.S. Pat. No. 4,120,946 discloses a pharmaceutical composition for barium opacification of the digestive tract, comprising colloidal barium sulfate and a polyacrylamide in an aqueous vehicle. The polyacrylamide forms a viscous solution at low concentration which makes it possible to maintain the barium sulfate in suspension and at the same time permit good adherence of the preparation to the walls of the organ which it is desired to x-ray.

U.S. Pat. No. 5,019,370 discloses a biodegradable radiographic contrast medium comprising biodegradable polymeric spheres which carry a radiographically opaque element, such as iodine, bromine, samarium and erbium. The contrast medium is provided either in a dry or liquid state and may be administered intravenously, orally and intraarterially.

While these polymeric materials greatly enhance attachment of the contrast agent used therewith to the walls of organs for better visualization thereof, they do not provide a uniform coating thereon. As such, there is still a need for an improved x-ray imaging medium that uniformly coats the soft tissues subjected to diagnostic x-ray examination.

It has now been discovered that high quality x-ray results can be obtained by utilizing a formulation comprising water-insoluble iodinated polymeric beads in combination with a cellulose derivative.

SUMMARY OF THE INVENTION

It is the object of the present invention to provide compositions for coating the gastrointestinal tract of mammals to form an effective radiopaque coating thereon by which diagnostic examination of the GI tract may be accomplished.

The object of the present invention is achieved by a composition comprising: water-insoluble iodinated polymeric beads as x-ray contrast agent in a pharmaceutically acceptable vehicle comprising a cellulose derivative.

In accordance with the invention there is further provided a method for x-ray diagnostic imaging of the GI tract which comprises orally or rectally administering to the patient an effective contrast producing amount of the above-described x-ray contrast compositions.

The iodinated polymeric beads are water-insoluble, non-water swellable in finely-divided form having a particle size of from about 0.01 to about 1000μ. The iodinated polymer from which the beads are produced by comminution or other techniques known in the art, has an iodine content in excess of 35 weight percent based on the weight of the polymer and contains repeating units of the formula:

$$\begin{array}{c} -\!\!\!\!\!(A)\!\!\!\!\!- \\ | \\ X \end{array} \qquad \mathrm{I}$$

wherein

A is a repeating organic unit in the backbone chain of the polymer, and

X is an organic moiety containing an iodinated aromatic group and a hydrophilic group, said moiety having an iodine content within the range of from about 40 to 80 weight percent based on the molecular weight of X.

A preferred embodiment of the invention features a crosslinked, iodinated polymer of formula I wherein A represents the residue of a repeating unit in the backbone chain of a polymer having appended hydroxyl groups, the hydroxyl groups providing crosslinking sites and reaction sites for attachment of the moiety X.

The cellulose derivative utilized in the present invention includes methylcellulose, carboxymethylcellulose, sodium carboxymethylcellulose, hydroxyethyl methylcellulose, hydroxypropyl methylcellulose; and microcrystalline cellulose having an average particle size of from 0.01 to 100μ, more preferably of from 0.05 to 10μ, and most preferably of 0.1 to 1μ.

The contrast agent and the cellulose derivative are formulated for administration using physiologically acceptable carriers or excipients in a manner within the skill of the art. The contrast agent and the cellulose derivative with the addition of pharmaceutically acceptable aids (such as surfactants and emulsifiers) and excipients are suspended in an aqueous medium resulting in a dispersion, suspension or emulsion.

A method for diagnostic imaging of the GI tract for use in medical procedures in accordance with this invention comprises orally or rectally administering to the mammalian patient in need of x-ray examination, an effective contrast producing amount of a composition of the present invention. After administration, at least a portion of the GI tract containing the administered composition is exposed to x-rays to produce an x-ray image pattern corresponding to the presence of the contrast agent, then the x-ray image is visualized and interpreted using techniques known in the art.

DETAILED DESCRIPTION OF THE INVENTION

Starting materials, reagents and solvents can be obtained from chemical suppliers, such as Aldrich, Baker, DuPont and Eastman Chemical Companies, or they may be prepared by techniques known in the prior art.

The water-insoluble iodinated polymeric beads utilized in the present invention are disclosed in U.S. Pat. No. 4,406,878, the disclosure of which is incorporated herein by reference.

The general structural formula of iodinated polymers of the invention is represented by structural formula I above. The backbone chain of the iodinated polymer can represent:

(i) a condensation polymer such as a polyester, polyamide, polyurethane, polycarbonate, polyepoxide, polyether, a phenolformaldehyde polymer and equivalent condensation polymers;

(ii) an addition polymer produced by the polymerization of one or more addition polymerizable monomers containing a polymerizable unsaturated double bond, e.g., vinyl monomers, including such addition polymers as poly(vinyl alcohol), poly(alkylmethacrylates), poly(alkylacrylates), and equivalent addition polymers; or (iii) a naturally occurring polymer, for example, a polysaccharide containing repeating glucose units such as starch, glycogen, cellulose, cellulosic derivatives, and equivalent naturally occuring polymers.

Preferably, repeating units A of formula I represents the residue of a repeating unit having an appended hydroxyl group, such as the repeating unit of poly (vinyl alcohol), the repeating epoxy unit of a polyepoxide, the repeating unit of a hydroxylated acrylic polymer such as poly (hydroxyethylacylate), or the repeating glucose unit of a naturally occurring polysaccharide. The appended hydroxyl group can serve either as a crosslinking site or as a reaction site for precursor compounds of the organic moiety X in formula I. Such precursor compounds can be chemically linked to the repeating units of the polymer backbone chain through a condensation reaction with the appended hydroxy group.

The organic moiety X of formula I above represents an iodine-containing organic fragment comprising an iodinated aromatic group and one or more hydrophilic groups. To obtain the high iodine content characteristic of the polymers used in the invention, the iodinated aromatic group have multiple iodine substituents bonded directly to the aromatic carbon ring atoms. Especially preferred among these iodinated aromatic groups are aromatic groups containing three, preferably four, carbon ring atoms substituted by iodine. A preferred iodinated aromatic group is an iodinated phenyl ring, although napthyl rings and nitrogen-containing heterocyclic rings containing 5 to 7 ring atoms can also be used. An especially preferred iodinated aromatic group is a phenyl ring bearing iodine substituents on a 4 of the carbon ring atoms.

The hydrophilic group(s) of X are typically present as a substituent(s) bonded directly, or indirectly through a chemical linking group, to one or more of the carbon ring atoms of the iodinated aromatic group. Preferred linking groups include short chain aliphatic groups, e.g., alkylene groups, amido groups and equivalent aliphatic groups, having 1 to 4 carbon atoms. Typically hydrophilic groups can be selected from a variety of such groups including carboxyl groups; sulfo groups; amino groups; salts thereof such as carboxylate salts, sulfonate salts, ammonium salts; polyols such as glucose groups; and equivalent hydrophilic groups.

Typically, the precursors from which the organic moiety X of formula I is derived contains a reactive group which forms a chemical linking group with the repeating unit of the polymer backbone chain. In the preferred embodiment of the invention wherein the repeating unit of the polymer backbone chain represents the residue of a repeating unit bearing a hydroxyl group, the reactive group contained on the precursor of X is a group reactive with the hydroxy group. For example, the reactive group can be a carboxyl group which condenses with the appended hydroxy group of the backbone chain to form an ester group linking an iodinated aromatic moiety of the polymer backbone. A variety of other reactive groups which react with a hydroxy group to form such chemical linking groups as ethers, amides, thioesters, carbonates, carbamates, sulfides, and equivalents, can also be used.

A partial listing of precursors for the moiety X of formula I includes, for example, 3-(3-amino-2,4,6-triiodophenyl)-2-ethylpropionic acid; 3-(3 -hydroxy-2,4,6-triiodophenyl)-2-ethylpropionic acid; sodium 3-(3-butyrylamino-2,4,6-triiodophenyl)-2-ethylacrylate; 3,5-diiodo-4-pyridone-N-acetic acid; 3-acetamido-2,4,6-triiodobenzoic acid; tetraiodophthalic anhydride; and the like. Tetraiodophthalic anhydride can be particularly useful because of its high iodine content.

Based on the foregoing description, a structural formula of certain preferred iodinated polymers can be illustrated as

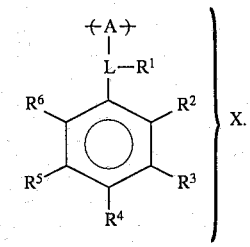

wherein:

A is as defined in formula I above;

X is as defined in formula I above;

L represents one of the above-described linking groups, e.g. ester, ether, amide, thioester, carbonate, carbamate, sulfide and the like; and each of $R^1$ to $R^6$ which may be the same or different, represents hydrogen, an iodine-containing substituent, or a hydrophilic group-containing substituent, with the proviso that the iodine content of X is from about 40 to 80 percent (based on the molecular weight of X).

Preferred iodinated polymers are crosslinked. This can enhance the water-insolubility and resistance to swell properties of the polymer. Crosslinking can be effected by incorporation of suitable crosslinking sites either on the polymer backbone chain or on the moiety X or both. For example, in a preferred embodiment wherein the polymer contains a repeating backbone unit bearing an appended hydroxyl group and a sidechain group A containing a carboxyl group as a hydrophilic group, a hydroxyl group appended to the backbone chain of one polymer can react with the carboxyl group attached to the sidechain X of another polymer, thereby crosslinking the two polymers through an ester linkage.

The polymeric contrast agents of the invention contain both hydrophilic and hydrophobic groups. Repeating backbone units A of formula I are substantially hydrophobic as are many portions of the moiety X. Of course X also contains one or more hydrophilic groups. This combination of hydrophobic and hydrophilic groups is believed important to provide the proper polymer surface and electrical characteristics which, in turn, provide proper polymer compatibility with body organs and tissues.

The iodinated polymers can be prepared by any of a variety of conventional polymerization and chemical reaction techniques. A preferred reaction sequence is to chemically react precursor compounds for the side-chain group X with a preformed polymer containing appended groups serving as suitable reaction sites, e.g., hydroxyl groups. The preformed polymer can be prepared by addition or condensation polymerization, depending on the polymer; or it can be obtained from naturally occurring sources in the case of naturally occurring polymers; e.g., polysaccharides. The precursor compounds for the moiety X can be reacted with the reaction site on the polymer backbone by a variety of well-known reaction procedures, depending on the nature of the linking group L in formula II above which is formed in this reaction. Advantageously, the reaction of these precursor compounds is carried out under emulsifying conditions so that the resultant polymers are obtained in finely-divided particulate form. Crosslinking can be carried out during or following attachment of the moiety X of the polymer backbone.

EXAMPLE 1

Five and one-half grams of poly (vinyl alcohol), PVA, purchased under the trademark Elvanol 52–22 from DuPont was swelled with stirring overnight in 300 ml of pyridine. The mixture was stirred for 4 days at room temperature with 65 g of tetraiodophthalic anhydride to react the PVA with the anhydride. The mixture was then heated to 60° C. for 8 hours to effect crosslinking. A copious precipitate of the iodinated polymeric reaction product formed. This was filtered off and washed with water and dried. Analysis showed that the polymeric reaction product has an iodine content of 61.7 percent compared with a theoretical value of 73.0 percent for complete reaction. The structure of a repeating unit of this iodinated polymeric reaction product was as follows:

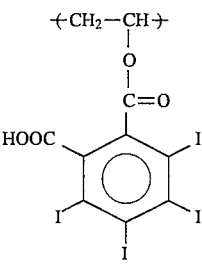

Having obtained a water-insoluble and non-water-swellable iodinated polymer as described above, the polymer can be subjected to grinding or milling treatment to obtain polymer particles of the appropriate size range. Of course, in cases where the polymers are prepared under suitable conditions, such as bead polymerization or emulsifying conditions, the polymers may already have an appropriate particle size so that additional milling or grinding may be unnecessary. A useful particle size for these polymer particles is within the range of from about 0.01 to 1000 microns, preferably 0.1 to 100 microns.

Compositions of the Present Invention

The contrast agents may be formulated for administration using physiologically acceptable carriers or excipients in a manner within the skill of the art. The contrast agents with the addition of pharmaceutically acceptable aids (such as surfactants and emulsifiers) and excipients may be suspended in an aqueous medium resulting in a dispersion, suspension or emulsion.

Compositions of the present invention comprise the following pharmaceutically acceptable components based on % w/v:

| Ingredients | Broad Range | Preferred Range |
| --- | --- | --- |
| Iodinated Polymeric Beads (% w/v) | 5–95 | 20–70 |
| Cellulose derivative (% w/v) | 0.05–10 | 0.1–4 |
| Surfactant (% w/v) | 0.1–20 | 3–7 |
| Viscosity modifying excipients (% w/v) | 0.001–4 | 0.05–1 |
| Water—q.s. to 100% by volume | | |

To stabilize particulates in the compositions of the present invention electrolytes may be used in the range of from about 0.01 to about 10% w/v based on the total composition. Such electrolytes include sodium chloride, potassium chloride, citric acid and salts thereof, phosphoric acid and salts thereof and aluminum chloride.

The preferred cellulose derivative utilized in the present invention is AVICEL® RC-591, which is a mixture of about 89 parts microcrystalline cellulose and about 11 parts of sodium carboxymethylcellulose.

In further reference to the components used in the compositions of the present invention the following should be noted.

The x-ray contrast agent present in concentrations lower than the above-stated minimum in formulations does not provide good quality x-ray or CT images, while concentrations above the maximum concentration render the GI tract too radiopaque and do not allow sufficient delineation of the GI tract.

While the iodinated polymeric beads of the present invention in formulations with a pharmaceutically acceptable vehicle provide good quality x-ray images, the addition of a cellulose derivative to the formulations greatly increases the quality of the x-ray images. At the low extreme of the concentration range there is little or no benefit gained, while above the higher extreme of the concentration range the dispersions/suspensions are too viscous for administration.

Depending on the form and amount of cellulose derivative used, additions of viscosity modifying agents may not be necessary; at higher levels than about 10% w/v the viscosity is too high and gels will tend to form.

The following formulation examples will further illustrate the invention.

EXAMPLE 2

| Components | Amounts in % w/v |
| --- | --- |
| Iodinated Polymeric Beads | 17.50 |
| Polysorbate 80 (Tween 80) | 3.37 |
| Sorbitan Mono-oleate (Span 80) | 1.64 |
| AVICEL ® RC-591 | 0.50 |
| q.s. with water to 100% by volume | |

EXAMPLE 3

| Components | Amounts in % w/v |
| --- | --- |
| Iodinated Polymeric Beads | 25.00 |
| Polysorbate 80 (Tween 80) | 5.00 |
| AVICEL ® RC-591 | 6.50 |
| q.s. with water to 100% by volume | |

EXAMPLE 4

| Components | Amounts in % w/v |
| --- | --- |
| Iodinated Polymeric Beads | 20.00 |
| Polysorbate 20 (Tween 20) | 5.00 |
| AVICEL ® RC-591 | 1.00 |
| q.s. with water to 100% by volume | |

EXAMPLE 5

| Components | Amounts in % w/v |
| --- | --- |
| Iodinated Polymeric Beads | 30.00 |
| Mineral Oil, NF | 10.00 |
| Polysorbate 80 (Tween 80) | 3.37 |
| Sorbitan Mono-oleate (Span 80) | 1.64 |
| AVICEL ® RC-591 | 0.50 |
| q.s. with water to 100% by volume | |

As known by those skilled in the art, surfactants or emulsifiers can reduce the interfacial tension between two immiscible phases, i.e., oil-in-aqueous medium. These agents can be used alone or in combination with other emulsifying agents and surfactants. For example, Dow Corning Medical Antifoam AF, which is a composition of 30% w/v polydimethylsiloxane simethicone and silica aerogel, 14% w/v stearate emulsifiers and 0.075% w/v sorbic acid, the balance being water, may be used by itself. Intralipid, which is an emulsion of fatty acids needs the presence of a suspending agent for it to form an acceptable emulsion with contrast agents of the present invention. The surface active agents may be cationic, anionic, nonionic, zwitterionic or a mixture of two or more of these agents.

Suitable cationic surfactants include cetyl trimethyl ammonium bromide. Suitable anionic agents include sodium lauryl sulphate, sodium heptadecyl sulphate, alkyl benzenesulphonic acids and salts thereof, sodium butylnapthalene sulfonate, and sulphosuccinates. Zwitterionic surface active agents are substances that when dissolved in water they behave as diprotic acids and, as they ionize, they behave both as a weak base and a weak acid. Since the two charges on the molecule balance each other out the molecules act as neutral molecules. The pH at which the zwitterion concentration is maximum is known as the isoelectric point. Compounds, such as certain amino acids having an isoelectric point at the desired pH of the formulations of the present invention are useful in practicing the present invention.

In preparing the formulations of the present invention we prefer to use nonionic emulsifiers or surface active agents which, similarly to the nonionic contrast agents, possess a superior toxicological profile to that of anionic, cationic or zwitterionic agents. In the nonionic emulsifying agents the proportions of hydrophilic and hydrophobic groups are about evenly balanced. They differ from anionic and cationic surfactants by the absence of charge on the molecule and, for that reason, are generally less of an irritant than the cationic or anionic surfactants. Nonionic surfactants include carboxylic esters, carboxylic amides, ethoxylated alkylphenols and ethoxylated aliphatic alcohols.

One particular type of carboxylic ester nonionic surface active agents are the partial, for example mono-, esters formed by the reaction of fatty and resin acids, for example of about 8 to about 18 carbon atoms, with polyhydric alcohols, for example glycerol, glycols such as mono-, di-, tetra- and hexaethylene glycol, sorbitan, and the like; and similar compounds formed by the direct addition of varying molar ratios of ethylene oxide to the hydroxy group of fatty acids.

Another type of carboxylic esters is the condensation products of fatty and resin partial acids, for example mono-, esters ethylene oxide, such as fatty or resin acid esters of polyoxyethylene sorbitan and sorbitol, for example polyoxyethylene sorbitan, monotall oil esters. These may contain, for example, from about 3 to about 80 oxyethylene units per molecule and fatty or resin acid groups of from about 8 to about 18 carbon atoms. Examples of naturally occurring fatty acid mixtures which may be used are those from coconut oil and tallow while examples of single fatty acids are dodecanoic acid and oleic acid.

Carboxylic amide nonionic surface active agents are the ammonia, monoethylamine and diethylamine amides of fatty acids having an acyl chain of from about 8 to about 18 carbon atoms.

The ethoxylated alkylphenol nonionic surface active agents include various polyethylene oxide condensates of alkylphenols, especially the condensation products of monoalkylphenols or dialkylphenols wherein the alkyl group contains about 6 to about 12 carbon atoms in either branched chain or particularly straight chain configuration, for example, octyl cresol, octyl phenol or nonyl phenol, with ethylene oxide, said ethylene oxide being present in amounts equal to from about 5 to about 25 moles of ethylene oxide per mole of alkylphenol.

Ethoxylated aliphatic alcohol nonionic surface active agents include the condensation products of aliphatic alcohols having from about 8 to 18 carbon atoms in either straight chain or branched chain configuration, for example oleyl or cetyl alcohol, with ethylene oxide, said ethylene oxide being present in equal amounts from about 30 to about 60 moles of ethylene oxide per mole of alcohol.

Preferred nonionic surface active agents include: sorbitan esters (sold under the trade name Span) having the formula:

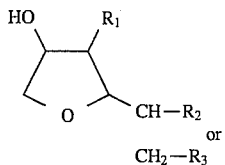

wherein $R_1=R_2=OH$, $R_3=R$ for sorbitan monoesters, $R_1=OH$, $R_2=R_3=R$ for sorbitan diesters, $R_1=R_2=R_3=R$ for sorbitan triesters, where $R=(C_{11}H_{23})$ COO for laurate, $(C_{17}H_{33})$ COO for oleate, $(C_{15}H_3)$ COO for palmitate, $(C_{17}H_{35})$ COO for stearate.

Polyoxyethylene alkyl ethers (i.e. Brijs) having the formula:

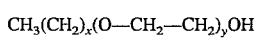

where $(x+1)$ is the number of carbon atoms in the alkyl chain, typically:

12 lauryl (dodecyl)

14 myristyl (tetradecyl)

16 cetyl (hexadecyl)

18 stearyl (octadecyl)

and y is the number of ethylene oxide groups in the hydrophilic chain, typically 10–60.

Polyoxyethylene sorbitan fatty acid esters (Polysorbates 20, 40, 60, 65, 80 & 85) sold under the trade names of Tweens, Crillers, Sorlares and Monitans, having the formulas (1) and (2)

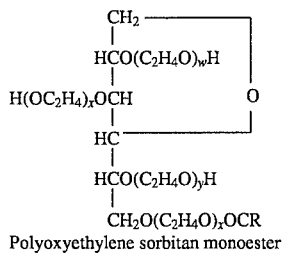

Polyoxyethylene sorbitan monoester

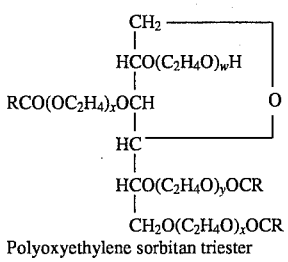

Polyoxyethylene sorbitan triester wherein $w+x+y+z=20$ (Polysorbate 20, 40, 60, 65, 80 and 85)

$w+x+y+z+=5$ (Polysorbate 81)

$w+x+y+z=4$ (Polysorbate 21 and 61).

Polyethylene stearates, such as:

poly(oxy-1,2-ethanediyl), α-hydro-ω-hydroxyoctadecanoate;

polyethylene glycol monostearate; and poly(oxy-1,2-ethanediyl)-α-(1-oxooctadecyl)-ω-hydroxypolyethylene glycol monostearate.

The dosages of the contrast agent used according to the method of the present invention will vary according to the precise nature of the contrast agent used. Preferably, however, the dosage should be kept as low as is consistent with achieving contrast enhanced imaging. By employing as small amount of contrast agent as possible, toxicity potential is minimized. For most contrast agents of the present invention dosages will be in the range of from about 0.1 to about 16.0 g iodine/kg body weight, preferably in the range of from about 0.5 to about 6.0 g iodine/kg of body weight, and most preferably, in the range of from about 1.2 to about 2.0 g iodine/kg body weight for regular x-ray visualization of the GI tract. For CT scanning, the contrast agents of the present invention will be in the range of from about 1 to about 600 mg iodine/kg body weight, preferably in the range of from about 20 to about 200 mg iodine/kg body weight, and most preferably in the range of from about 40 to about 80 mg iodine/kg body weight.

The concentration of the contrast agent should be in the range of from about 5% w/v to about 95% w/v of the formulation, preferably from about 20% w/v to about 70% w/v, and most preferably of from about 25% w/v to about 50% w/v.

The invention having been fully described, it will be apparent to one skilled in the art that changes and modifications can be made thereto without departing from the spirit and scope thereof.

What is claimed is:

1. An x-ray contrast composition for oral or retrograde examination of the gastrointestinal tract comprising:

(a) from about 5 to 95% w/v of iodinated polymeric, water-insoluble beads having a particle size of from about 0.01 to about 1000μ wherein said iodinated polymeric beads comprise a polymer containing repeating units of the formula (I)

   I wherein

A is a repeating organic unit in the backbone chain of the polymer; and

X is an organic moiety containing an iodinated aromatic group and a hydrophilic group, said moiety having an iodine content within the range of from about 40 to about 80 weight percent based on the molecular weight of X;

(b) from 0.05 to 10% w/v of a cellulose derivative selected from the group consisting of microcrystalline cellulose;

(c) from 0.1 to 20% w/v of a surfactant selected from the group consisting of nonionic, anionic, cationic and zwitterionic surfactants;

(d) from 0.001 to 4% w/v of a viscosity modifying excipient; and (e) water to make 100% by volume.

2. The x-ray contrast composition of claim 1 wherein X represents an organic moiety containing an iodinated aromatic group, said moiety being of the formula

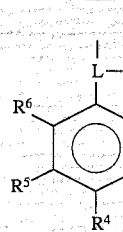

wherein

L represents a linking group selected from the class consisting of ester groups, ether groups, amide groups, thioester groups, carbonate groups, carbamate groups, and sulfide groups; and each of $R^1$ to $R^6$, which may be the same or different, represents hydrogen, an iodine-containing substituent, or a hydrophilic group-containing substituent, with the provisos that (i) the iodine content of X is within the range of from 40 to 80 wt %; and (ii) said hydrophilic group is a member selected from the class consisting of carboxyl groups, sulfo groups, amino groups, salts of the aforementioned carboxyl, sulfo and amino groups, and polyol groups.

3. The x-ray contrast composition of claim 1 wherein said surfactant constitutes from 3 to 7% of the composition.

4. The x-ray contrast composition of claim 1 wherein said microcrystalline cellulose has an average particle size of from 0.01 to 100μ.

5. The x-ray contrast composition of claim 4 wherein said microcrystalline cellulose is about 89 parts microcrystalline cellulose and about 11 parts of sodium carboxymethylcellulose.

6. The x-ray contrast composition of claim 1 wherein said nonionic surface active agent is selected from the group consisting of carboxylic esters, carboxylic amides, ethoxylated alklyphenols and ethoxylated aliphatic alcohols.

7. The x-ray contrast composition of claim 1 wherein said surfactant is sorbitan ester having the formula:

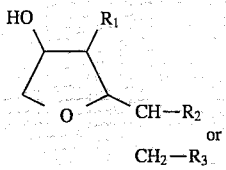

wherein
$R_1=R_2=OH$, $R_3=R$ for sorbitan monoesters,
$R_1=OH$, $R_2=R_3=R$ for sorbitan diesters,
$R_1=R_2=R_3=R$ for sorbitan triesters,
where
$R=(C_{11}H_{23})$ COO for laurate, $(C_{17}H_{33})$ COO for oleate, $(C_{15}H_{31})$ COO for palmitate or $(C_{17}H_{35})$ COO for stearate.

8. The x-ray contrast composition of claim 1 wherein said surface active agent is polyoxyethylene alkyl ether having the following formula:

$$CH_3(CH_2)_x(O-CH_2-CH_2)_yOH$$

where (x+1) is the number of carbon atoms in the alkyl chain, and y is the number of ethylene oxide groups in the hydrophilic chain, from about 10 to about 60.

9. The x-ray contrast composition of claim 1 wherein said surfactant is polyoxyethylene sorbitan fatty acid ester of the formulas (1) and (2)

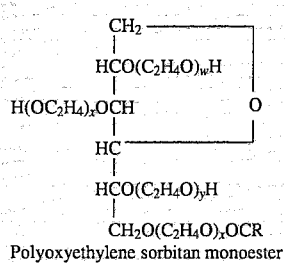
Polyoxyethylene sorbitan monoester

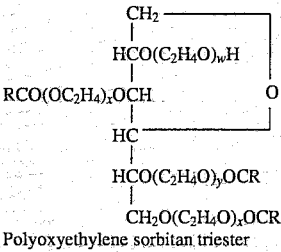
Polyoxyethylene sorbitan triester wherein the sum w+x+y+z is equal to 4, 5 or 20.

10. The x-ray contrast composition according to claim 8, wherein the alkyl chain is selected from the group consisting of lauryl (dodecyl), myristyl (tetradecyl), cetyl (hexadecyl) and stearyl (octadecyl).

11. A method of carrying out x-ray examination of the gastrointestinal tract of a patient, said method comprises the oral or rectal administration to the patient an x-ray contrast formulation comprising:

(a) from about 5 to 95% w/v of iodinated polymeric, water-insoluble beads having a particle size of from about 0.01 to about 1000μ wherein said iodinated polymeric beads comprise a polymer containing repeating units of the formula (I)

     I wherein

A is a repeating organic unit in the backbone chain of the polymer; and

X is an organic moiety containing an iodinated aromatic group and a hydrophilic group, said moiety having an iodine content within the range of from about 40 to about 80 weight percent based on the molecular weight of X;

(b) from 0.05 to 10% w/v of a cellulose derivative selected from the group consisting of microcrystalline cellulose;

(c) from 0.1 to 20% w/v of a surfactant selected from the group consisting of nonionic, anionic, cationic and zwitterionic surfactants;

(d) from 0.001 to 4% w/v of a viscosity modifying excipient; and (e) water to make 100% by volume.

12. The method of claim 11 wherein

X represents an organic moiety containing an iodinated aromatic group, said moiety being of the formula

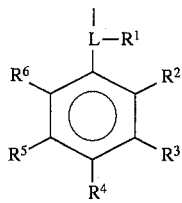

wherein

L represents a linking group selected from the class consisting of ester groups, ether groups, amide groups, thioester groups, carbonate groups, carbamate groups, and sulfide groups; and each of $R^1$ to $R^6$, which may be the same or different, represents hydrogen, an iodine-containing substituent, or a hydrophilic group-containing substituent, with the provisos that (i) the iodine content of X is within the range of from 40 to 80 wt %; and (ii) said hydrophilic group is a member selected from the class consisting of carboxyl groups, sulfo groups, amino groups, salts of the aforementioned carboxyl, sulfo and amino groups, and polyol groups.

13. The method of claim 11 wherein said surfactant constitutes from 3 to 7% of the composition.

14. The method of claim 10 wherein said microcrystalline cellulose has an average particle size of from 0.01 to 100μ.

15. The method of claim 14 wherein said microcrystalline cellulose is about 89 parts microcrystalline cellulose and about 11 parts of sodium carboxymethylcellulose.

16. The method of claim 11 wherein said nonionic surface active agent is selected from the group consisting of carboxylic esters, carboxylic amides, ethoxylated alklyphenols and ethoxylated aliphatic alcohols.

17. The method of claim 11 wherein said surfactant is sorbitan ester having the formula:

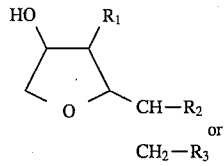

wherein
$R_1=R_2=OH$, $R_3=R$ for sorbitan monoesters,
$R_1=OH$, $R_2=R_3=R$ for sorbitan diesters,
$R_1=R_2=R_3=R$ for sorbitan triesters,
where
$R=(C_{11}H_{23})$ COO for laurate, $(C_{17}H_{33})$ COO for oleate, $(C_{15}H_{31})$ COO for palmitate or $(C_{17}H_{35})$ COO for stearate.

18. The method of claim 11 wherein said surface active agent is polyoxyethylene alkyl ether having the following formula:

$$CH_3(CH_2)_x(O-CH_2-CH_2)_yOH$$

wherein (x+1) is the number of carbon atoms in the alkyl chain, and y is the number of ethylene oxide groups in the hydrophilic chain, from about 10 to about 60.

19. The method of claim 11 wherein said surfactant is polyoxyethylene sorbitan fatty acid ester of the formulas (1) and (2)

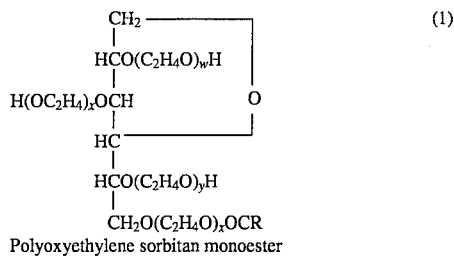

Polyoxyethylene sorbitan monoester

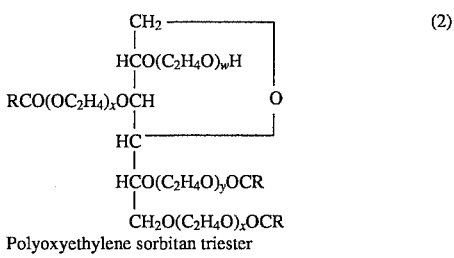

Polyoxyethylene sorbitan triester wherein the sum w+x+y+z is equal to 4, 5 or 20.

20. The x-ray contrast composition of claim 13, wherein the cellulose derivative further comprising at least one of the group consisting of methylcellulose, carboxymethylcellulose, sodium carboxymethylcellulose, hydroxyethyl methylcellulose, and hydroxypropyl methylcellulose.

21. The method according to claim 11, wherein the cellulose derivative further comprises at least one of the group consisting of methylcellulose, carboxymethylcellulose, sodium carboxymethylcellulose, hydroxyethyl methylcellulose, and hydroxypropyl methylcellulose.

22. The method according to claim 11 wherein the microcrystalline cellulose has an average particle size of from 0.01 to 100 microns.

23. The method according to claim 22 wherein the cellulose derivative comprises about 89 parts microcrystalline cellulose and about 11 parts of sodium carboxymethylcellulose.

24. The method according to claim 18, wherein the alkyl chain is selected from the group consisting of lauryl (dodecyl), myristyl (tetradecyl), cetyl (hexadecyl) and stearyl (octadecyl).

* * * * *